United States Patent [19]

Mains et al.

[11] 4,421,112

[45] Dec. 20, 1983

[54] TIBIAL OSTEOTOMY GUIDE ASSEMBLY AND METHOD

[75] Inventors: Douglas B. Mains, Wheaton, Ill.; Kenneth E. Merte, Stillwater, Minn.

[73] Assignee: Minnesota Mining and Manufacturing Company, St. Paul, Minn.

[21] Appl. No.: 380,412

[22] Filed: May 20, 1982

[51] Int. Cl.³ .......................... A61F 5/04; A61B 17/18
[52] U.S. Cl. ................................ 128/92 EB; 128/83; 128/92 E; 128/303 R; 128/305
[58] Field of Search .............. 128/303 R, 303 B, 305, 128/305.1, 310, 317, 92 E, 92 A, 92 EA, 92 EB, 83; 33/174 D

[56] References Cited

U.S. PATENT DOCUMENTS

| 1,201,467 | 10/1916 | Hoglund . | |
|---|---|---|---|
| 2,200,120 | 5/1940 | Nauth | 128/83 |
| 2,500,370 | 3/1950 | McKibbin | 128/92 EB |
| 2,697,433 | 12/1954 | Zehnder | 128/92 EB |
| 2,737,724 | 3/1956 | Herz | 128/92 EB X |
| 3,073,310 | 1/1963 | Mocarski | 128/303 B |
| 3,135,263 | 6/1964 | Connelley, Jr. | 128/303 B |
| 3,486,500 | 12/1969 | Ball et al. | 128/83 X |
| 3,814,089 | 6/1974 | Deyerle | 128/92 EB |
| 4,230,117 | 10/1980 | Anichkov | 128/303 B |
| 4,325,373 | 4/1982 | Slivenko et al. | 128/303 R |
| 4,335,715 | 6/1982 | Kirkley | 128/92 EB |
| 4,349,018 | 9/1982 | Chambers | 128/92 E |

OTHER PUBLICATIONS

"A Jig for Pin Insertion in the Performance of High Tibial Osteotomy" by F. G. Lippert et al., *Clinical Orthopaedics and Related Research*, Oct. 1975, vol. 112, pp. 242–244.

"The Saab Jig: An Aid in High Tibial Osteotomy", Published in *Acta Orthopaedic Scandinavica*, 1978, vo. 49, pp. 85–88.

*Primary Examiner*—Ronald L. Frinks
*Attorney, Agent, or Firm*—Donald M. Sell; James A. Smith; Robert W. Hoke, II

[57] ABSTRACT

A method and guide assembly for use in a tibial osteotomy wherein two pairs of parallel guide pins are inserted into the tibia at a predetermined angle with respect to each other through a guide block. The adjacent surfaces of the pairs of pins are then used to precisely guide a saw by which a wedge-shaped segment of the tibia is removed.

11 Claims, 5 Drawing Figures

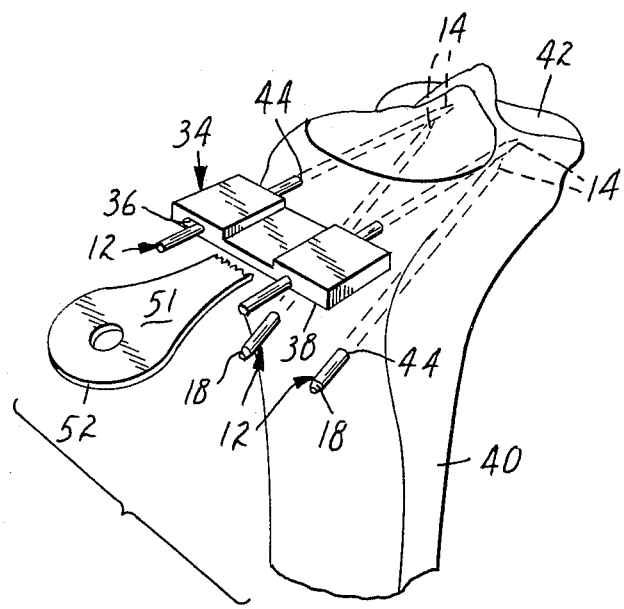
FIG.3
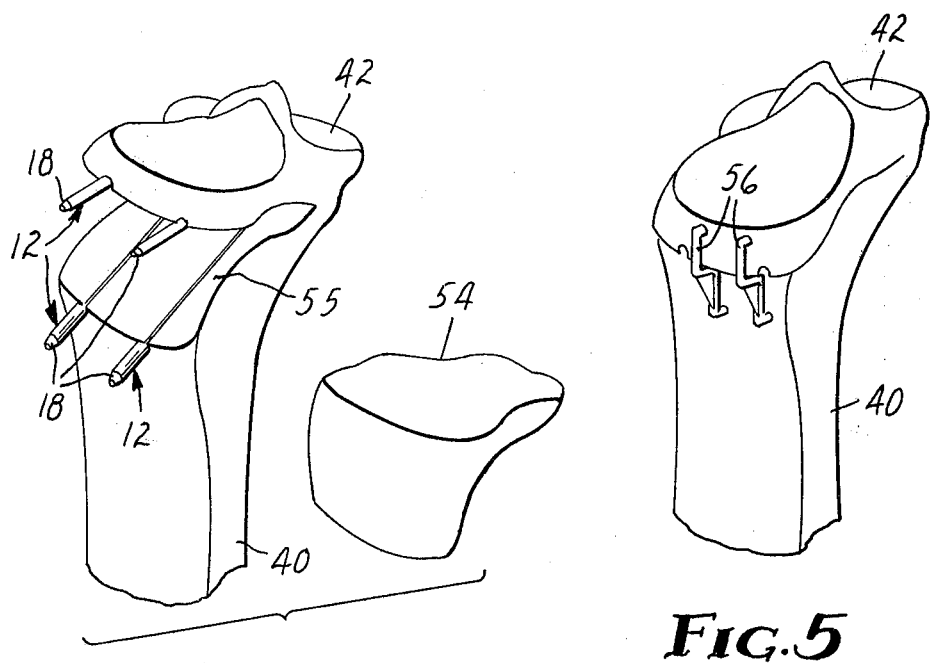
FIG.4
FIG.5

TIBIAL OSTEOTOMY GUIDE ASSEMBLY AND METHOD

TECHNICAL FIELD

This invention relates to assemblies and methods for removing wedge-shaped segments of bone, and particularly to such assemblies and methods for removing such a segment from a tibia just below a knee joint.

BACKGROUND ART

One known method for correcting varus (bow-legged) or valgus (knock-kneed) deformities in the tibia includes removing a wedge-shaped segment of the tibia extending generally transversely almost completely across the tibia just below the knee joint, bending the tibia to close the space left by removal of the segment, fastening the tibia in its bent position and allowing the bone to heal in that position. Such a method, if properly done, can relieve painful knee conditions caused by disproportionate loading of one side of the knee joint due to such deformities. Achieving the proper orientation of the tibia for such relief, however, requires thorough study of the leg structure to determine the shape and orientation of the segment to be removed, and removal of a segment of precisely the predetermined shape and orientation. Otherwise any relief obtained may be only temporary.

One prior art osteotomy guide for use in removing such a segment guides the path of a saw that cuts the wedge-shaped segment from a guide structure attached to the side of the tibia. Such a guide is bulky and thus difficult to precisely locate, however; and affords no positive way of checking after it is attached to be sure that the wedge that will be removed by its use will be removed precisely from the desired location on the tibia.

Another prior art osteotomy guide for use in removing such a segment comprises two guide pins, including a first pin adapted to be inserted into the tibia just below and generally parallel to the plane of the knee joint, and a second pin adapted to be inserted into the tibia at an angle with respect to the first pin corresponding to the dihedral angle of the wedge-like segment desired to be removed. The surgeon guides the flat surface of an oscillating saw along the adjacent surfaces of the pins to cut the wedge-shaped segment from the tibia. The location of such guide pins can be checked by X-ray devices to be sure that they are accurately placed. Each pin makes only line contact with a planar side surface of the saw that it guides, however, so that the saw can cut along a number of different planes tangent to the surface of each pin, each of which planes will result in a slightly different dihedral angle for the segment removed, and a different orientation of the line of intersection of the cutting planes that define the hinge line about which the tibia is bent after the segment is removed. Thus it is easily possible to cut out and remove a segment that affords more or less correction than is desired, and that results in the tibia being bent in a sagittal plane as well as a longitudinal plane of the body, which may not be a desired result.

DISCLOSURE OF THE INVENTION

The present invention provides a tibial osteotomy guide assembly and method for use in correcting varus (bowlegged) or valgus (knock-kneed) deformities via removal of a wedge-shaped segment of the tibia, which guide assembly and method provide an accurate dihedral angle and location for the segment of bone removed from the tibia that can be checked before the segment is actually removed so that the desired corrective result may be more accurately obtained.

The method for performing a tibial osteotomy according to the present invention comprises the steps of first inserting a first pair of parallel guide pins in the tibia just below the knee joint so that the intersection of a plane through the axes of both pins with a sagittal plane of the body is generally parallel to the plane of the knee joint, and the intersection of the plane through the axis of both pins with a longitudinal plane of the body is generally parallel to or angled generally away from the plane of the knee joint starting from the point of insertion of the pins. Next, a second pair of parallel guide pins is inserted in the tibia below the first pair, which second pair of guide pins is disposed at a predetermined angle with respect to the first pair of pins so that planes tangent to and defined by the surfaces of each pair of guide pins adjacent the other pair of guide pins will intersect within the tibia adjacent its cortical shell on the side of the tibia opposite the side from which the pins are inserted with the line of intersection between these intersecting planes being generally along a sagittal plane of the body. An oscillating saw blade is then guided along the surfaces of each pair of guide pins adjacent the other pair of guide pins to cut a wedge-shaped segment from the tibia along those intersecting planes. The segment and pairs of guide pins are removed from the tibia, the cortical shell of the tibia is bent generally about an axis defined by the line of intersection of those planes to close the space left by the removed segment and bring the newly severed surfaces into face-to-face engagement, the tibia is fastened in that bent condition and the newly severed surfaces are allowed to heal together.

With two parallel guide pins serving as guides for each cut of the saw, it is relatively easy for the surgeon to accurately cut a wedge of a shape and location dictated by the position of the pins, and the location of the pins can be checked after they are inserted and before cutting begins through the use of an X-ray device.

Preferably the pins each have a cutting end surface adapted to cut bone tissue upon rotation of the guide pin about its axis with the cutting end surface pressed against the bone tissue so that the pins can be inserted in the manner of a drill through the use of a drill motor; and the pins are accurately located through the use of a guide block having a first pair of spaced parallel guide bores adapted to closely receive and guide the first pair of guide pins as they are inserted into the tibia and a second pair of spaced parallel guide bores adapted to receive and guide the second pair of guide pins as they are inserted. The second pair of parallel guide bores is oriented to direct the second pair of guide pins as they are inserted so that a second plane tangent to and defined by the surfaces of the second pair of guide pins adjacent the first pair of pins will intersect a first plane tangent to and defined by the surfaces of the first pair of pins adjacent the second pair of pins at a predetermined angle and at a second predetermined distance from a locating surface of the guide block, and a first predetermined distance related to the second predetermined distance (such as by being the same distance) is marked along the length of at least the first pair of guide pins. Thus after the first pair of guide pins is inserted a desired depth into the tibia through the guide block (which depth can be determined by feeling the emergence of the tips of the pins through the curved cortical shell of the tibia), the guide block is located along the first pair of guide pins with the locating surface of the block at a relationship with respect to the locating mark along at least one of the first pair of pins that will, in the surgeon's judgment, leave an appropriate portion of the cortical shell adjacent the apex of the bone segment to be removed to act as a hinge about which the tibia can be bent. The guide block is then fixed in this position against movement toward the tibia by means on the locating block, which means may be in the form of an adjustment member adjustably mounted in the guide block for movement in a direction generally parallel to the first pair of guide bores that has an end surface adapted to engage the surface of the tibia positioned on the side of the block toward which the bores converge.

The second pair of guide pins are then inserted into the tibia through the second pair of guide bores, the guide block is removed by either breaking the block at a thin section between the pairs of guide bores or breaking off the projecting parts of at least one pair of the pins, and the side surfaces of the pins remaining in the tibia are used to guide the side surface of an oscillating saw cutting the segment from the tibia in the manner described above. Such guiding of the saw can be facilitated through the use of a guide plate having parallel through openings spaced and shaped to slidably engage either pair of guide pins located by the locating block, and having a planar surface essentially tangent to its through openings (and thus the plane defining surfaces of the engaged pair of guide pins) along which the saw blade is guided as it enters the tibia.

Preferably the guide block has a plurality of second pairs of guide bores, each second pair being adapted to receive the second pair of guide pins and being oriented to direct the second pair of guide pins so that the second plane defined by the second pair of guide pins will intersect the first plane defined by the first pair of guide pins at a different predetermined angle at the second predetermined distance from the surface on the block. Thus the same guide block will allow a surgeon a choice of dihedral angles for the segment of tibia to be removed.

BRIEF DESCRIPTION OF THE DRAWING

The invention will be further described with reference to the accompanying drawing wherein like numbers refer to like parts in the several views, and wherein:

FIGS. 2 through 5 are perspective views sequentially illustrating a method according to the present invention which isuses the guide assembly of FIG. 1 to remove a wedge-shaped segment from a tibia.

DETAILED DESCRIPTION

Figure 1:
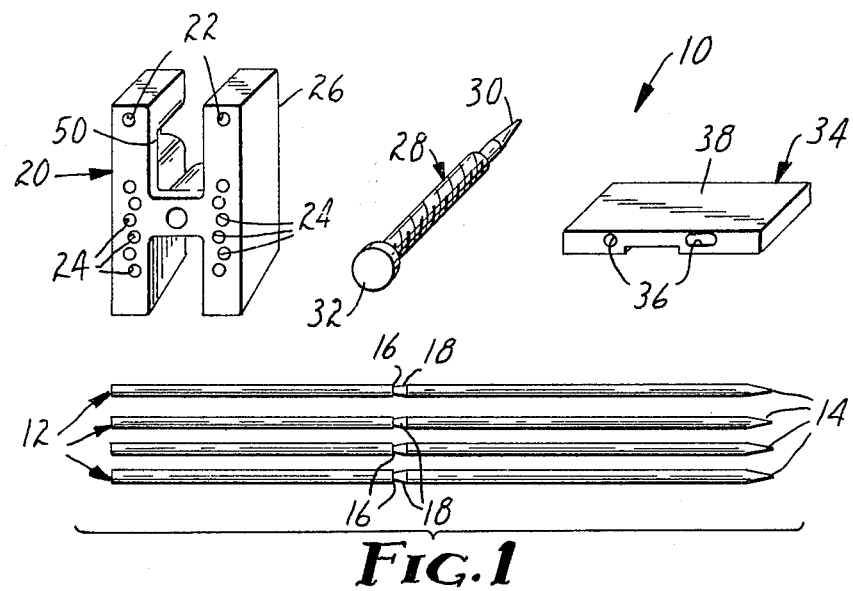
FIG. 1 is a view, partially in perspective, of a tibial osteotomy guide assembly according to the present invention.

Referring now to the drawing there is shown in FIG. 1 a tibial osteotomy guide assembly according to the present invention generally designated by the reference numeral 10.

The guide assembly 10 comprises four generally cylindrical guide pins 12 of a suitable material, such as stainless steel, each having a cutting end surface 14 which may be of any suitable shape such as fluted or V-shaped as illustrated, and is adapted to cut bone tissue upon rotation of the guide pin about its axis with the cutting end surface 14 pressed against the bone tissue. At least two, and as illustrated, all of the guide pins 12 have locating marks the same first predetermined distance from the tips of the cutting end surfaces 14, which marks are defined by shoulders 16 adjacent frustro-conical pin portions 18 which afford breaking the pins 12 at the shoulder 16 for reasons that will later be explained.

The guide assembly 10 also includes a guide block 20 of a suitable material such as stainless steel or a ridged polymeric material. The guide block 20 has a first pair of spaced parallel guide bores 22 adapted to closely receive a first pair of the guide pins 12 and a plurality of second pairs of spaced parallel guide bores 24 adapted to receive the other or second pair of guide pins 12. Each of the second pairs of parallel guide bores 24 is oriented to direct the second pair of guide pins 12 so that a second plane tangent to and defined by the surfaces of the second pair of guide pins 12 adjacent the first pair of guide pins 12 will intersect a first plane tangent to and defined by the surfaces of the first pair of guide pins 12 adjacent the second pair of guide pins 12 at a different predetermined angle (e.g., angles of from 7½ to 20 degrees in 2½ degree increments) at a second predetermined distance from a side locating surface 26 of the guide block 20 through which the bores 22 and 24 open, and on the side of the block toward which the bores 22 and 24 converge. The first predetermined distance between tips of the end surface 14 and the shoulders or marks 16 on the guide pins 12 and this second predetermined distance have a known relationship to each other to facilitate use of the assembly 10, which relationship in the illustrated assembly is that both distances are the same.

An adjustment member 28 is adjustably mounted in the guide block 20 by being threadably engaged therewith for movement in a direction generally parallel to the first pair of guide bores 22. The adjustment member 28 has a conical end surface 30 adapted to engage the surface of a bone positioned on the side of the block 20 toward which the bores 22 and 24 converge, and has a knurled manually engageable knob 32 at its end opposite its end surface 30 by which the spacing between the end surface 30 and block locating surface 26 may be adjusted for reasons to be explained later.

Also the guide assembly 10 includes a saw guide plate 34 having parallel through openings 36 spaced and shaped to slidably receive either the first or second pair of guide pins 12 located by the bores 22 and 24 of the guide block 20. The plate 34 has a planar guide surface 38 essentially tangent to both openings 36 through the guide plate which can be used to guide an oscillating saw during use of the guide assembly 10 as will later be explained.

Figure 2:
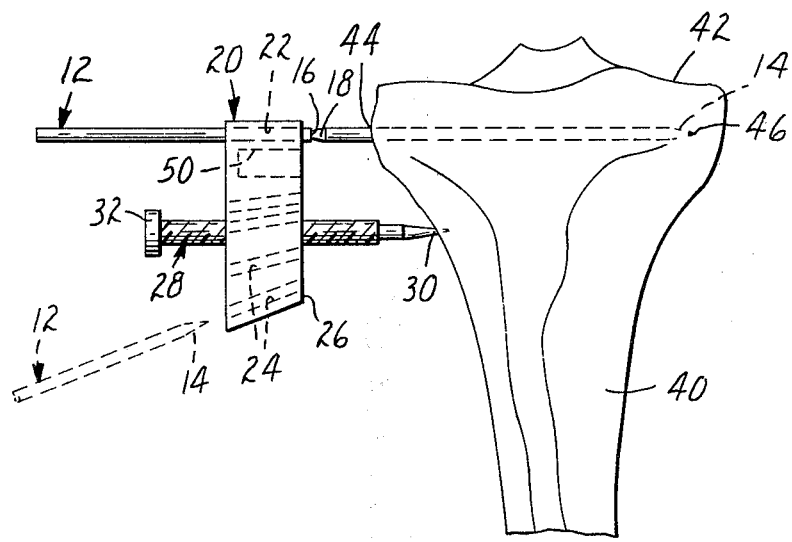

The method according to the present invention for performing a tibial osteotomy through the use of the guide assembly 10 will now be explained with reference to FIGS. 2 through 4. First, (FIG. 2) the first pair of the guide pins 12 is inserted in a tibia 40 just below a knee joint 42 by rotating the pins 12 via a drill motor (not shown) through the first pair of bores 22 in the guide block 20 located so that the intersection of a plane through the axes of both pins 12 with a sagittal plane of the body is generally parallel to the plane of the knee joint 42, and the intersection of the plane through the axis of both pins 12 with a longitudinal plane of the body is generally parallel to or angled generally away from the plane of the knee joint 42 starting from the point 44 of insertion of the first pair of pins 12. The depth of insertion of the first pair of pins 12 is determined by feeling for the emergence of the tips of the pins 12 through the curved cortical shell of the tibia, such as at location 46. The guide block 20 is then located along the pins 12 with the locating surface 26 of the block 20 at a relationship with respect to the shoulder 16 or mark along at least one of the first pair of pins 12 that will, in the surgeon's judgment, leave an appropriate portion of the cortical shell of the tibia 40 adjacent the apex of the bone segment to be removed to act as a hinge about which the tibia 40 can be bent (the surgeon being mindful in such locating that the planes along which the cuts will be made will intersect at the tip of the guide pin 12 if the locating surface 26 is aligned with the mark 16 on the pin 12, or will intersect at the same distance and direction from the tip of the guide pins 12 that the locating surface 26 is positioned from the mark 16). The guide block 20 is then fixed in that position against movement toward the tibia 40 by manually rotating the adjustment member 28 via the knob 32 to place its end surface 30 against the side surface of the tibia 40. Next, the second pair of pins 12 is inserted into the tibia 40 disposed at a predetermined angle with respect to the first pair of pins 12 by inserting them through a preselected pair of the bores 24 so that the first and second planes defined by the adjacent surfaces of the two pairs of pins 12 will intersect within the tibia 40 adjacent its cortical shell on the side of the tibia 40 opposite the side from which the pins 12 are inserted with the line of intersection being generally parallel to a sagittal plane of the body. The location of the pins 12 and thus the planes can then be checked by an X-ray device, and the guide pins 12 can be relocated if necessary.

The guide block 20 is then removed by either breaking the block 20 at a thin section 50 between the pairs of guide bores 22 and 24 or breaking off the projecting parts of at least one pair of the pins 12 at the shoulder 16; and any remaining guide pins 12 that still have their original length are shortened to prevent their interference with the sawing operation by either breaking them at the shoulder 16, or severing them with a cutting tool (not shown).

The saw guide plate 34 is then placed over one pair of pins 12 (FIG. 3) with the pins 12 in its openings 36 and its guide surface 38 adjacent the other pair of pins 12; and a side surface 51 of an oscillating saw blade 52 driven by a suitable motor (not shown) is guided first along the guide surface 38 and then along the surfaces of both guide pins 12 to make a cut along the pins 12 from the outer surface of the tibia 40 to adjacent the intersection of the first and second planes defined by the pins 12. After such a cut via the use of the guide plate 34 is made along the planes defined by the adjacent surfaces of both sets of pins 12, a wedge-shaped segment 54 of the tibia 40 is removed (FIG. 4) and any excess bone tissue at the apex of the wedge-shaped groove formed by the saw blade 52 is removed through the use of an osteotome or chisel. The pins 12 are then removed by either pulling them axially out of the tibia 40 or breaking them through the newly severed surface on the tibia 40, the cortical shell of the tibia 40 is bent (FIG. 5) adjacent the apex of the wedge-shaped groove to close the opening left by removing the segment 54 (which normally causes a "green twig" fracture in that portion of the cortical shell), the newly severed surfaces 55 are secured in face-to-face relationship as by staples 56, plates or other means, and the newly severed surfaces of the tibia 40 are allowed to heal together.

As will be appreciated by those skilled in the art, many variations of the method and osteotomy guide assembly described above may be used without departing from the spirit of the present invention. For example, while as described and illustrated the first predetermined distance between the tips of the locating pins 12 and the marks 16 on the locating pins 12 is the same as the second predetermined distance from the locating surface 26 to the intersection of the second plane defined by the second pair of locating pins 12 with the plane defined by the first pair of locating pins 12, these two predetermined distances need not be the same, but only need to have a known relationship. The second predetermined distance could be shorter than the first predetermined distance by a known amount that would leave an appropriate amount of the cortical shell to act as a hinge for bending the tibia 40 when the tips of the first pair of pins 12 are aligned at the outer surface of that shell and the mark 16 is positioned at the locating surface. Also, the guide assembly and method may be useful for removing wedge shaped segments from bones other than the tibia, such as from the femur, if desired to correct bone shapes. Thus the scope of the present invention should not be limited to the structures and steps described herein, but only by the structures and steps recited in the dependent claims and their equivalents.

We claim:

1. An osteotomy guide assembly comprising: four guide pins, each having a cutting end surface adapted to cut bone tissue upon rotation of said guide pin about its axis with said cutting end surface pressed against said tissue, at least two of said guide pins having a locating mark a first predetermined distance from said cutting end surface;

a guide block having a first pair of spaced parallel guide bores adapted to closely receive the two of said guide pins having said locating marks, and a second pair of spaced parallel guide bores adapted to receive the other two of said guide pins, said second pair of parallel guide bores converging with respect to said first pair and being oriented to direct the guide pins extending through the second bores so that a second plane tangent to and defined by the surfaces of the second pair of pins adjacent the first pair of pins will intersect a first plane tangent to and defined by the surfaces of the first pair of pins adjacent the second pair of pins at a predetermined angle and at a second predetermined distance from a locating surface on said guide block; said second predetermined distance having a known relationship to said first predetermined distance; and means mounted on said guide block for fixing the position of said guide block along said first pair of pins against movement toward a surface positioned on the side of said block toward which said bores converge.

2. A guide assembly according to claim 1 wherein said guide block has a plurality of second pairs of guide bores, each pair being adapted to receive the other two of said guide pins and being oriented to direct guide pins extending therethrough so that the second plane defined by those guide pins will intersect said first plane at a different predetermined angle at said second predetermined distance from said locating surface on said block.

3. A guide assembly according to claim 1 or claim 2 wherein said block has a thin cross section between said first and second pairs of guide bores affording severing of said block through said cross section.

4. A guide assembly according to claim 1 or claim 2 wherein said means for fixing comprises an adjustment member adjustably mounted in said guide block for movement in a direction generally parallel to said first pair of guide bores, said adjustment member having an end surface adapted to engage said surface positioned on the side of said block toward which said bores converge.

5. A guide assembly according to claim 4 wherein said adjustment member is threadably engaged in said block.

6. A guide assembly according to claim 1 or claim 2 further including a guide plate having parallel through openings spaced and sized to slidably engage either of said pairs of guide pins located by said pairs of bores in said guide block, said guide plate having a planar saw guide surface essentially tangent to both openings through said guide block.

7. A guide assembly according to claim 1 wherein said first and second predetermined distances are the same.

8. A method for performing a tibial osteotomy to correct varus and valgus deformities comprising the steps of:

inserting a first pair of parallel guide pins in the tibia just below the knee joint so that the intersection of a plane through the axes of both guide pins with a sagittal plane of the body is generally parallel to the plane of the knee joint, and the intersection of the plane through the axis of both pins with a longitudinal plane is generally parallel to or angled generally away from the plane of the knee joint starting from the point of insertion of the guide pins;

inserting a second pair of parallel guide pins in the tibia below the first pair and disposing the second pair of guide pins at a predetermined angle with respect to the first pair of guide pins so that a second plane tangent to and defined by the surfaces of the second pair of guide pins adjacent the first pair of pins will intersect a first plane tangent to and defined by the surfaces of the first pins adjacent the second plane within the tibia adjacent its cortical shell on its side opposite the side from which the pins are inserted at a line of intersection generally parallel to a sagittal plane of the body;

guiding an osteotomy saw blade along first one and then the other of the pairs of guide pins on their surfaces adjacent the other pair of guide pins to cut a wedge-shaped segment from the tibia;

removing the segment and the pairs of guide pins from the tibia;

bending the tibia about the line of intersection of the planes to close the space provided by the removed segment; and fastening the tibia in the bent condition.

9. A method according to claim 8 wherein said first and second pairs of guide pins are inserted by the use of a guide block, and said method includes the steps of fixing the guide block against movement toward the tibia between said inserting steps, and severing the pins or the guide block to afford removal of the guide block after both of said inserting steps and prior to said guiding step.

10. A method according to claim 9 wherein said method further includes the step of checking the location of the guide pins by using an X-ray device after said inserting step and prior to said guiding step.

11. A method for performing an osteotomy to correct deformities comprising the steps of:

inserting a first pair of parallel guide pins in the bone;

inserting a second pair of parallel guide pins in the bone adjacent the first pair and disposing the second pair of guide pins at a predetermined angle with respect to the first pair of guide pins so that a second plane tangent to and defined by the surfaces of the second pair of guide pins adjacent the first pair of pins will intersect a first plane tangent to and defined by the surfaces of the first pins adjacent the second plane within the bone adjacent its cortical shell on its side oppoiste the side form which the pins are inserted;

guiding an osteotomy saw blade along first one and then the other of the pairs of guide pins on their surfaces adjacent the other pair of guide pins to cut a wedge-shaped segment from the bone;

removing the segment and the pairs of guide pins from the bone;

bending the bone about the line of intersection of the planes to close the space provided by the removed segment; and fastening the bone in the bent condition.

* * * * *